United States Patent
Wyart et al.

(10) Patent No.: US 10,731,182 B2
(45) Date of Patent: Aug. 4, 2020

(54) METHANOGEN SUBSTRATE FOR BIOGAS PRODUCTION

(71) Applicant: ROQUETTE FRERES, Lestrem (FR)

(72) Inventors: Herve Wyart, Cuinchy (FR); Mathias Ibert, La Chapelle d'armentieres (FR)

(73) Assignee: ROQUETTE FRERES, Lestrem (FR)

(*) Notice: Subject to any disclaimer, the term of this patent is extended or adjusted under 35 U.S.C. 154(b) by 818 days.

(21) Appl. No.: 15/313,328

(22) PCT Filed: May 26, 2015

(86) PCT No.: PCT/FR2015/051387
§ 371 (c)(1),
(2) Date: Nov. 22, 2016

(87) PCT Pub. No.: WO2015/181490
PCT Pub. Date: Dec. 3, 2015

(65) Prior Publication Data
US 2017/0145442 A1 May 25, 2017

(30) Foreign Application Priority Data
May 26, 2014 (FR) ...................... 14 54715

(51) Int. Cl.
*C12P 5/02* (2006.01)
*C07D 493/04* (2006.01)
*C07D 307/20* (2006.01)
*C08G 65/34* (2006.01)
*C12N 1/20* (2006.01)

(52) U.S. Cl.
CPC ............ *C12P 5/023* (2013.01); *C07D 307/20* (2013.01); *C07D 493/04* (2013.01); *C08G 65/34* (2013.01); *C12N 1/20* (2013.01); *Y02E 50/343* (2013.01)

(58) Field of Classification Search
None
See application file for complete search history.

(56) References Cited

U.S. PATENT DOCUMENTS

2004/0110994 A1* 6/2004 Bhatia .................. C07D 493/04
568/845
2007/0125369 A1 6/2007 Olson et al.

FOREIGN PATENT DOCUMENTS

| EP | 1149805 | 10/2001 |
| WO | 03089435 | 10/2003 |
| WO | 2012083149 | 6/2012 |

OTHER PUBLICATIONS

Polaert et al. Chem. Eng. J. (2013) 222: 228-239 (Year: 2013).*
Rose et al: "Isosorbide as a Renewable Platform chemical for Versatile Applications-Quo Vadis?", ChemSusChem, vol. 5, No. 1, Jan. 9, 2012, pp. 167-176, XP055035243.
Kuhn et al.: "Catabolism of 1,5-Anhydro-D-Fructose in Sinorhizobium morelense S-30.75: Discovery, Characterization, and Overexpression of a New 1,5-Anhydro-D-Fructose Reductase and Its Application in Sugar Analysis and Rare Sugar Synthesis", Applied and Enviromental Microbiology, vol. 72, No. 2, Feb. 1, 2005, pp. 1248-1257, XP055164240.
Fleche et al.: "Preparation, Properties and Chemistry", Staerke-Starch, Wiley-VCH Verlag, Weinheim, DE, vol. 38, Jan. 1, 1986, pp. 26-30, XP001062256.
Meng et al., "Impact Factors and Optimization of the Methanogenic Conditions of Anaerobic Digestions with Glucose Substrate," Guangdong Agricultural Sciences, vol. 2014-08, pp. 139-144 (2014).

* cited by examiner

Primary Examiner — Susan M Hanley
(74) Attorney, Agent, or Firm — Oliff PLC

(57) ABSTRACT

The use of a product for internal dehydration of hydrogenated sugar as a methanogen substrate in a method for biogas production, a composition including a monoanhydrohexitol (M), a dianhydrohexitol (D), and anhydrohexitol polymers (P), and a methanisation method.

17 Claims, No Drawings

METHANOGEN SUBSTRATE FOR BIOGAS PRODUCTION

FIELD OF THE INVENTION

A subject of the invention is the use of a product of internal dehydration of a hydrogenated sugar for biogas production. A subject of the invention is also a specific composition that can be obtained by internal dehydration of a hydrogenated sugar and that is very useful as a methanization substrate. Another subject of the invention relates to a methanization process using said product of internal dehydration of a hydrogenated sugar.

PRIOR ART

With the reduction in gas resources, the increase in the cost of extracting said gases and the development of the sensitivities of public opinion to sustainable development, processes for producing biogas, that can be obtained from resources that are renewable over a short time, have been the subject of very considerable interest over the past 20 years.

Biogas is obtained by methanization (also known as anaerobic digestion) of organic matter. The degradation is carried out by microorganisms, under controlled conditions and the absence of oxygen. At the end of this degradation, biogas and a wet product rich in partially stabilized organic matter, called a digestate, are recovered.

This digestate can be used for manure spreading, optionally after a composting step.

With regard to the biogas obtained, it generally comprises mainly methane, carbon dioxide and a few trace gases such as dinitrogen, ammonia and hydrogen sulfide. With regard to the latter two, it is preferable to limit their content in the biogas as much as possible. This is because, during combustion of the biogas, the ammonia will easily be converted into nitrogen oxides (NOx) which are dangerous to humans and to the environment. As for hydrogen sulfide, it is a corrosive and toxic gas. Furthermore, when hydrogen sulfide is burnt, it is converted into sulfur oxides (SOx) and then, in the environment, into sulfuric acid or other sulfates, the latter being to a large extent responsible for the acid rain phenomenon.

It is possible to obtain biogas from many types of organic matters or "biomasses", for example biomasses of food-processing, agricultural or municipal origin. This may in particular be liquid manure, fats or else waste from the food-processing industry. Each biomass has a defined methane potential, which represents the volume of methane that can be obtained from a given mass of this biomass. The higher the methane potential, the better the methane productivity of this biomass.

By way of example, mention may be made of document EP 1 149 805 A1, which describes a process for producing biogas from waste of biomass type, this waste possibly coming in particular from sugar beet. This process comprises a step of pretreating the waste which consists of a step of dehydrating the waste. According to said document, the term dehydration is intended to mean reducing the moisture content to approximately 30%. The advantage of this process is that the concentrated biomass can be stored, under nitrogen, for a long period (from 6 to 8 months) without this biomass beginning to ferment. Thus, this process has the advantage of being able to use the biomass, the production of which is by nature seasonal, throughout the year. However, this process has the drawback of requiring the dehydrated biomass to be stored under nitrogen.

Said document does not describe chemical modification of the waste used, but only a reduction in its moisture content before use in methanization.

Thus, it still remains necessary, at the current time, to find a methanizable organic matter, also called "methanogenic substrate" in the remainder of the description. This methanogenic substrate has a high methane potential, which can be higher than that of other substrates already known, such as liquid manures or glucose. It is advantageous for this methanogenic substrate to be sufficiently stable to be able to be methanized after long-term storage, for example after storage for several months, this being even in a non-controlled atmosphere. It is also preferable for the methanogenic substrate to produce a biogas free of, or comprising small amounts of, ammonia and/or hydrogen sulfide.

SUMMARY OF THE INVENTION

This is precisely the subject of the present invention which relates to the use of a product of internal dehydration of a hydrogenated sugar as a methanogenic substrate in a biogas production process.

The invention also relates to a composition which comprises, relative to its dry matter:
 up to 50% of at least one monoanhydrohexitol (M) and of at least one dianhydrohexitol (D);
 at least 50% of anhydrohexitol polymers (P);
 the sum of the constituents (M)+(D)+(P) coming to 100% and said constituents M and D being present according to an M/(M+D) weight ratio ranging from 0.40 to 0.95.

This specific composition can in particular be used for biogas production since it is an excellent methanogenic substrate.

A subject of the invention is also a methanization process comprising:
 a step of introduction, into a digester, of a methanogenic substrate comprising a product of internal dehydration of a hydrogenated sugar, in the presence of a microorganism, so as to form a methanogenic medium;
 a step of anaerobic digestion of the methanogenic substrate at a temperature ranging from 15 to 70° C., preferably from 25 to 45° C., in order to form a biogas;
 a step of recovery of said biogas, this step possibly being carried out throughout the digestion step.

DETAILED DESCRIPTION OF THE INVENTION

An object of the invention is to provide a novel methanogenic substrate that is useful in biogas production processes.

The term "methanogenic substrate" is intended to mean a substrate capable of producing methane during its biodegradation under anaerobic conditions.

Unless otherwise indicated in the description which follows, all the percentages are expressed by weight.

In the context of studies on biomass exploitation, the applicant has been able to observe that this product of internal dehydration of a hydrogenated sugar is of great interest in methanization. This is because this product is stable over time when it is stored in a closed manner, but is capable of being degraded anaerobically. Its methane potential is particularly advantageous, in comparison with other methanogenic substrates such as liquid manures or glucose. Moreover, the digestate obtained has, for its part, a biodegradable nature.

Preferably, the product of internal dehydration of a hydrogenated sugar comprises an anhydrohexitol, an anhydrohexitol polymer or a mixture of these products, the anhydrohexitol preferably being chosen from dianhydrohexitols such as isosorbide, isomannide, isoidide, or monoanhydrohexitols such as sorbitans, mannitans and iditans and/or any mixtures of at least two of these products. Preferably, the product of internal dehydration of a hydrogenated sugar is a product of internal dehydration of sorbitol.

A monoanhydrohexitol is a reaction product of a single internal dehydration of hexitol. A dianhydrohexitol is a reaction product of a double internal dehydration of hexitol. An anhydrohexitol polymer is a reaction product of intermolecular dehydration between a monoanhydrohexitol or a dianhydrohexitol and one or more products chosen from monoanhydrohexitol, dianhydrohexitol and hexitol.

Preferably, the product of internal dehydration of a hydrogenated sugar has, relative to its dry matter, an amount of sulfur of less than 3%, advantageously an amount of sulfur of less than 2%, preferentially from 5 ppm to 1.5% of sulfur, for example from 10 ppm to 0.8% of sulfur.

The use of this substrate having these controlled amounts of sulfur makes it possible to produce a biogas which has a low concentration, or even a zero amount, of hydrogen sulfide.

According to the invention, the product of internal dehydration of a hydrogenated sugar is used as a methanogenic substrate together with at least one additional methanogenic matter different than the product of internal dehydration of a hydrogenated sugar. The additional methanogenic matter may be waste of agricultural, food-processing, industrial, household or municipal origin.

The product of internal dehydration of a hydrogenated sugar has the advantage of being able to be combined with numerous other methanogenic matters. Its compatibility with the latter allows a great versatility when it is used for biogas production.

Preferably, the product of internal dehydration of a hydrogenated sugar is a mixture which comprises, relative to its dry matter:
  up to 50% of at least one monoanhydrohexitol (M) and of at least one dianhydrohexitol (D), for example from 5% to 50%, in particular from 10% to 50%, advantageously from 25% to 45%, preferably from 30% to 40%;
  at least 50% of anhydrohexitol polymers (P), for example from 50% to 95%, in particular from 50% to 90%, advantageously from 55% to 75%, preferentially from 60% to 70%;
  the sum of the constituents (M)+(D)+(P) coming to 100% and said constituents M and D being present according to an M/(M+D) weight ratio ranging from 0.40 to 0.95, advantageously from 0.42 to 0.90, preferably from 0.45 to 0.85.

This specific product of internal dehydration of a hydrogenated sugar, which is a mixture of monoanhydrohexitols, of dianhydrohexitols and of anhydrohexitol polymers, has the advantage of being stable over time, while at the same time having a biodegradable nature and a particularly advantageous methane potential. The invention thus also relates to this specific composition.

In the example of application WO 03/089435, a continuous isosorbide production process is described. According to this process, a stream of by-products comprising isosorbide, sorbitans and anhydrosorbitol polymers is purified by adding water for the purpose of causing the insoluble anhydrosorbitol polymers to precipitate, in such a way as to recycle the isosorbide and the sorbitans in the process; the insoluble polymers are for their part removed from the process. In said document, nothing indicates that compounds M and D are found in this precipitate, even in trace amount.

The weight amounts in the dehydration product can be determined by gas chromatography (GC) as described hereinafter in the examples section.

This specific composition can be obtained by means of a production process comprising:
  a step of introducing at least one hexitol into a reactor in the presence of a dehydration catalyst;
  a step of dehydrating the hexitol so as to form a composition of monoanhydrohexitols (M), dianhydrohexitols (D) and anhydrohexitol polymers (P), which is rich in anhydrohexitol polymers;
  an optional step of neutralizing or eliminating the catalyst;
  a step of distilling the composition so as to reduce the amount of dianhydrohexitol (D);
  a step of recovering the composition having a reduced amount of dianhydrohexitols.

In the first step, the hexitol introduced into the reactor may be sorbitol, iditol or mannitol or a mixture of these polyols.

Simultaneously, before or after the introduction of hexitol, the dehydration catalyst is introduced into the reactor. This catalyst may be of any type, provided that it allows dehydration of the hexitol in the subsequent step. This catalyst may be a heterogeneous catalyst or a homogeneous catalyst. It may be an acid catalyst, in particular a strong acid catalyst, or an ion exchange resin, in particular acidic cation exchange resins, or acidic zeolite-type catalysts.

The acid catalyst may in particular be sulfuric acid, hydrochloric acid, para-toluenesulfonic acid, phosphoric acid or methanesulfonic acid.

Sulfuric acid is a catalyst that is particularly preferred for the production of the composition according to the invention.

The acidic cation exchange resin may be a sulfonated polystyrene resin such as the AG50W-X12 resin from Bio-Rad. The acidic zeolite may be a beta-zeolite.

The dehydration catalyst is introduced in amounts which allow the dehydration step to be carried out. In particular, when sulfuric acid is used, it is preferable to use amounts of less than 2% by weight relative to the total weight of hexitol, preferably less than 1.5%, most preferentially less than 1.2%.

The dehydration step can be carried out under vacuum, under a stream of an inert gas, for example nitrogen, or else under pressure in an autoclave, these three methods making it possible to facilitate the elimination of the water and thus to shift the reaction equilibrium.

In order to carry out the dehydration step, it is necessary to provide the reactor with heat. This amount of heat required depends mainly on the nature and the amount of catalyst used and, to a lesser extent, on the pressure conditions in the reactor during the dehydration step.

This dehydration step is carried out under conditions which allow the formation of a composition rich in anhydrohexitol polymers.

In order to provide the required heat, the temperature inside the reactor can range from 110 to 400° C. depending on the catalyst used. For example, when 1% by weight of sulfuric acid is used, relative to the weight of hexitol introduced, a temperature greater than or equal to 135° C., advantageously greater than or equal to 150° C., is preferably used. A temperature of less than 300° C. is also advantageously used with this catalyst used in these amounts.

At the end of the reaction, a composition of monoanhydrohexitols, dianhydrohexitols and anhydrohexitol polymers, which is rich in anhydrohexitol polymers, is obtained. The term "composition which is rich in anhydrohexitol polymers" is generally intended to mean a composition comprising at least 10% of these polymers, preferably at least 15%.

At the end of this dehydration step, this intermediate composition generally comprises, relative to its dry weight:
- 65% to 75% by weight of dianhydrohexitols (D);
- 5% to 15% by weight of monoanhydrohexitols (M), preferably from 8% to 12%;
- 10% to 25% by weight of anhydrohexitol polymers (P), preferably from 15% to 22%.

At the end of the dehydration step, when a homogeneous acid catalyst is used, a step of neutralizing the catalyst is preferably carried out.

A distillation step is then carried out so as to reduce the amount of dianhydrohexitol in such a way that the M/(M+D) weight ratio ranges from 0.40 to 0.95, this being whether, relative to its dry weight, the composition comprises up to 50% of monoanhydrohexitols (M) and of dianhydrohexitols (D).

This step can be carried out in any type of still which allows the dianhydrohexitols to be isolated. This step is carried out under vacuum, temperature and time conditions which allow the dianhydrohexitols to be isolated from the rest of the constituents of the composition.

By way of example, the distillation can be carried out, until the dianhydrohexitol no longer distills, at 50 mbar and at a temperature of 250° C. or else at 5 mbar and at a temperature of 200° C.

The product of internal dehydration of a hydrogenated sugar that is useful in the invention, and in particular the composition according to the invention, can have a Brookfield viscosity, according to a test A, included in the range of from 200 to 2000 mPa.s, preferably from 250 to 1800 mPa.s, most preferentially from 380 to 1200 mPa.s, the test A consisting in adjusting the dry matter of the composition to 85% and then measuring the Brookfield viscosity at 60° C. of the resulting composition.

The composition having the viscosity according to the invention has a consistency which allows it to be easily handled in biogas production processes and also to be easily anaerobically digested by microorganisms.

Advantageously, the product of internal dehydration of a hydrogenated sugar has a methane potential greater than 20 milliliters of methane per gram ($mLCH_4/g$) of dry matter of said product, advantageously greater than 50 $mLCH_4/g$, preferably greater than 110 $mLCH_4/g$, most preferentially greater than 130 $mLCH_4/g$, even more preferentially greater than 150 $mLCH_4/g$.

Thus, the methanogenic capacity or methane potential is greater than other known methanogenic substrates such as liquid manures or glucose.

Preferably, the product of internal dehydration of a hydrogenated sugar comprises isosorbide in a weight amount, relative to the total weight of dianhydrohexitols (D), of at least 90% by weight, advantageously at least 95%.

Preferably, the weight percentage of 1,4-sorbitan optionally present in the product of internal dehydration of a hydrogenated sugar is, relative to the total amount of monoanhydrohexitols, less than 10%, preferably less than 7%.

Advantageously, the composition according to the invention has a dry matter ranging from 50% to 100%. The dry weight can range from 60% to 95%, preferentially from 65% to 90%; the composition according to the invention can thus be in liquid form. When the composition has a dry matter of less than 100%, it also comprises a solvent which has a boiling point at atmospheric pressure of less than 150° C., which is generally water.

This composition has the additional advantage of being concentrated and thus of being able to be easily transported, before being optionally diluted in a solvent, for example water, so as to be possible for it to be used. The composition likewise also has, in the variant where it is in liquid form, the capacity to be easily handleable.

The composition generally has, according to a test B, a freezing point of less than 10° C., preferentially less than –5° C., most preferentially less than –20° C., the test B consisting in adjusting the dry matter of said composition to 85% and in measuring the freezing point of the composition with the dry matter thus adjusted. The present composition likewise also has, in this preferred variant, the capacity to be able to be easily stored, even at low temperature, before use.

The composition according to the invention which has excellent stability can also be used in other applications, for example for industrial applications. It can be used as a combustible agent, as a binder for agglomerating mineral fillers or plant fillers, for forming for example granules such as wood pellets, or else as a dye.

A subject of the invention is also a methanization process comprising:
- a step of introduction, into a digester, of a methanogenic substrate comprising a product of internal dehydration of a hydrogenated sugar, in the presence of a microorganism, so as to form a methanogenic medium;
- a step of anaerobic digestion of the methanogenic substrate at a temperature ranging from 15 to 70° C., preferably from 25 to 45° C., in order to form a biogas;
- a step of recovery of said biogas, this step possibly being carried out throughout the digestion step.

Before the first step of introduction into the digester, the methanogenic substrate can undergo any type of pretreatment. It can also be mixed with organic or inorganic matters conventionally used for biogas production. However, the methanogenic substrate comprising a product of internal dehydration of a hydrogenated sugar, as previously described, can be used as it is, without prior modification.

The digester used may be of any type. Said digesters may be batchwise digesters, which are similar to simple thermostated tanks, or else continuous facilities, for instance that described in document WO 2009/044076. By way of example, an infinitely mixed reactor, optionally combined with a decanter, a sludge bed or a fluidized bed or a piston reactor may be used. These reactors may be stirred by agitation, by recirculation of the biogas or by mechanical stirring.

The microorganism that is useful in the process of the invention is chosen from conventional microorganisms for biogas production. They are in particular microorganisms that are effective for anaerobic digestion of residues from the sugar or starch industries. These microorganisms may be psychrophilic (it is considered that they are then particularly effective at a temperature ranging from 15 to 25° C.), mesophilic (it is considered that they are then particularly effective at a temperature ranging from 25 to 45° C.) or thermophilic (it is considered that they are then particularly effective at a temperature ranging from 45 to 70° C.). The term "effective" is intended to mean that the bacterial population will have a tendency to grow, under anaerobic digestion conditions, after the substrate has been introduced into the digester. Preferably, a mesophilic microorganism is used and the temperature of the digester is thermostated at a temperature ranging from 20 to 50° C., most preferentially from 25 to 45° C.

Preferably, the dry matter of the methanogenic medium ranges from 0.1% to 50%, advantageously from 1% to 45%.

The product of internal dehydration of a hydrogenated sugar that is useful in the invention, and in particular the composition according to the invention, has the advantage of being able to be both dry-methanized and liquid-methanized.

It is also possible to introduce a buffer solution into the methanogenic medium in order to carry out the anaerobic digestion step. This makes it possible to limit excess production of volatile fatty acids.

Preferably, a solution of trace elements and/or a solution of macroelements is (are) introduced into the methanogenic medium for carrying out the anaerobic digestion step so as to improve the bacterial activity of the methanogenic medium. The solution of trace elements may comprise iron, cobalt, manganese, nickel, zinc, boron, selenium, copper and/or molybdenum, these trace elements being for example in the form of $FeCl_2$, $CoCl_2$, $MnCl_2$, $NiCl_2$, $ZnCl_2$, $H_3B0_3$, $Na_2SeO_4$, $CuCl_2$ and $Na_2Mo_4$. The solution of macroelements may comprise nitrogen, potassium, phosphorus, magnesium and/or calcium, for example in the form of $NH_4Cl$, $KH_2PO_4$, $MgCl_2$ and $CaCl_2$.

The digestion step has a duration that is sufficient to produce the biogas, which can range up to 8 weeks, preferably from 1 to 6 weeks.

The biogas recovered comprises essentially methane and carbon dioxide and a few trace gases such as dinitrogen, ammonia and hydrogen sulfide. By using the methanogenic substrate according to the invention, and in particular in its preferred variants, the biogas comprises very small amounts of ammonia, generally less than 10 ppm, and of hydrogen sulfide, generally less than 3000 ppm, preferentially less than 2000 ppm.

The biogas recovered can also be withdrawn by subsequent purification methods that are already known. These methods can consist of a cycle of compression and decompression of the biogas, a cycle of heating and cooling of the biogas, passing the biogas through membranes or filters, for example active carbons, or a combination of these methods. These treatments make it possible to separate the methane from the other gases. The biogas withdrawn can be used in combustion or else be injected into mains gas circuits.

The digestate can then be spread, optionally after a re-treatment step, in particular a composting step.

The invention will now be illustrated in the examples hereinafter. It is specified that these examples do not in any way limit the present invention.

EXAMPLES

Operating techniques
Gas Chromatography

The weight proportions of monoanhydrohexitols (M), dianhydrohexitols (D) and anhydrohexitol polymers (P) contained in the compositions according to the invention are determined by gas chromatography.

The sample can be prepared according to the following method:

The weighings are always to be adjusted according to the sample to be analyzed. Weigh out respectively 60, 200 and 600 mg of sample and 50 mg of internal standard (methyl alpha-D-glucopyranoside) into 3 beakers of 100 ml. Add 50 ml of pyridine. Leave to stir magnetically until complete dissolution. Take up 1 ml of solution in a pot and add 0.3 ml of bis(trimethylsilyl) trifluoroacetamide. Stopper, stir and then heat for 30 minutes at 70° C. before injecting 1.5 microliters. The monoanhydrohexitols and dianhydrohexitols to be analyzed are then in the form of trimethylsilylated derivatives.

To produce the chromatogram, use is made of a Varian 3800 chromatograph equipped:

with a column of DB1 type having a length of 30 m and a diameter of 0.32 mm with a film thickness of 1 μm;
with a split-splitless injector heated to 300° C. using a constant helium flow rate of 1.7 mL/min;
Injection mode: split with "liner split";
with an FID detector heated to a temperature of 300° C.;
Column temperature: temperature programming as soon as injection from 140° to 250° C. at a rate of 3° C./minute and then up to 300° C. at a rate of 10° C./min.

The monoanhydrohexitols and the dianhydrohexitols are determined by their retention time relative to that of the internal standard. The quantification of the various compounds eluted is carried out by the internal calibration method.

Using the chromatogram, it is possible to calculate the weight percentage of each of the constituents by determining the surface area of the corresponding peaks, then by calculating the ratio of the surface area of the peak of the constituent to the surface area of the peak of the internal standard and finally by multiplying this ratio by the ratio of the weight of internal standard introduced into the beaker to the weight of sample introduced into the beaker; the result obtained is then divided by the coefficient of response of each constituent. The amounts of anhydrohexitol polymer (P) are calculated by difference to 100% with the amounts of monoanhydrohexitols (M) and dianhydrohexitols (D) previously determined.

Preparation of Compositions Useful to the Invention

In order to illustrate the invention and the advantages thereof, five compositions were produced according to the following protocols:

Example 1

1 kg of a solution of sorbitol at 70% of DM sold by the applicant under the name Neosorb® 70/02 and 7 g of concentrated sulfuric acid are placed in a jacketed stirred reactor. The mixture obtained is heated under vacuum (pressure of approximately 100 mbar) at 150° C. for 5 hours so as to eliminate the water contained in the initial reaction medium and that originating from the sorbitol dehydration reaction.

The reaction crude is then cooled to 100° C. and then neutralized with 11.4 g of a 50% sodium hydroxide solution. The dianhydrohexitol composition thus neutralized is then distilled under vacuum (pressure less than 50 mbar) at a temperature of 200° C. so as to discharge the majority of the dianhydrohexitol (D) formed. 130 g of a sorbitol internal dehydration composition 1, which comprises monoanhydrohexitol (M), dianhydrohexitol (D) that has not been distilled and also the anhydrohexitol polymer (P), is recovered in the round-bottomed flask. The water content of the composition obtained, determined by Karl-Fisher analysis, is less than 0.5%. This composition 1 is then analyzed by gas chromatography to determine the content of monoanhydrohexitols (M), dianhydrohexitols (D) and anhydrohexitol polymers (P). Thus, composition 1 obtained contains 28.2% of monoanhydrohexitols (M) and 8.6% of dianhydrohexitols (D)

relative to the dry matter, which corresponds to an anhydrohexitol polymer (P) content of 63.2%. The M/(M+D) ratio is equal to 28.2/(28.2+8.6), i.e. 0.77. The 1,4-sorbitan content is 4.5%, relative to the total amount of the monoanhydrohexitols, and the isosorbide content is 96% relative to the total amount of dianhydrohexitols.

The sulfur content of composition 1, determined by ICP (plasma torch) analysis, is equal to 1.05%. The Brookfield viscosity of composition 1 according to the test B, after adjusting to 85% of dry matter, is equal to 450 mPa.s. The freezing point of composition 1 measured according to the test B, after adjusting to 85% of dry matter, is less than −20° C.

Example 2

Example 1 is reproduced except for the fact that the distillation is carried out at 190° C. 145 g of a composition 2 which contains 26.1% of monoanhydrohexitol (M) and 16.4% of dianhydrohexitols (D), relative to the dry matter, which corresponds to an anhydrohexitol polymer (P) content of 57.5%, are recovered. The M/(M+D) ratio is equal to 26.1/(26.1+16.4), i.e. 0.61. The 1,4-sorbitan content is 3.5%, relative to the total amount of the monoanhydrohexitols, and the isosorbide content is 99.3% relative to the total amount of dianhydrohexitols. The sulfur content of composition 2 is equal to 0.9%.

The Brookfield viscosity of composition 2 according to the test B, after adjusting to 85% of dry matter, is equal to 420 mPa.s. The freezing point of composition 2 measured according to the test B, after adjusting to 85% of dry matter, is less than −20° C.

Example 3

Example 1 is reproduced except for the fact that the reaction is carried out at 140° C. and the distillation is carried out at 190° C. 204 g of a composition 3 which contains 40.9% of monoanhydrohexitol (M) and 13.5% of dianhydrohexitols (D), relative to the dry matter, which corresponds to an anhydrohexitol polymer (P) content of 45.6%, are recovered. The M/(M+D) ratio is equal to 40.9/(40.9+13.5), i.e. 0.75. The 1,4-sorbitan content is 4.7%, relative to the total amount of the monoanhydrohexitols, and the isosorbide content is 97.6% relative to the total amount of dianhydrohexitols. The sulfur content of composition 3 is equal to 0.75%. The Brookfield viscosity of composition 3 according to the test B, after adjusting to 85% of dry matter, is equal to 350 mPa.s. The freezing point of composition 3 measured according to the test B, after adjusting to 85% of dry matter, is less than −20° C.

Example 4

Example 1 is reproduced except for the fact that the reaction is carried out at 145° C. and the distillation is carried out at 190° C. 178 g of a composition 4 which contains 21.9% of monoanhydrohexitol (M) and 16.7% of dianhydrohexitols (D), relative to the dry matter, which corresponds to an anhydrohexitol polymer (P) content of 61.4%, are recovered. The M/(M+D) ratio is equal to 21.9/(21.9+16.7), i.e. 0.57.

Example 5

Example 1 is reproduced except for the fact that the reaction is carried out at 145° C. and the distillation is carried out at 185° C. 200 g of a composition 5 which contains 19.1% of monoanhydrohexitol (M) and 27.3% of dianhydrohexitols (D), relative to the dry matter, which corresponds to an anhydrohexitol polymer (P) content of 53.6%, are recovered. The M/(M+D) ratio is equal to 19.1/(19.1+27.3), i.e. 0.41.

All the compositions of examples 1 to 5 are useful in the invention as methanogenic substrates.

The compositions of examples 1, 2, 4 and 5 comprise amounts of anhydrohexitol polymers and an M/(M+D) weight ratio that are greater than those of the composition of example 3. These compositions 1, 2, 4 and 5 are preferred compositions of the invention.

Methanization Tests

The compositions of examples 1, 2 and 3 were evaluated in methanization. Beforehand, they are diluted to obtain compositions with a dry matter of 80% for easier handling of the product.

For this, the following protocol, adapted from standard 11734, is used:

1—Flask Preparation:

The mixture is composed of:

an inoculum, which is sludges comprising mesophilic microorganisms, derived from an industrial methanizer treating waste from the sugar industry; the amount of organic matter provided to the medium by the inoculum is about 10g/L;

solutions of trace elements ($FeCl_2$, $CoCl_2$, $MnCl_2$, $NiCl_2$, $ZnCl_2$, $H_3BO_3$, $Na_2SeO_4$, $CuCl_2$, $Na_2Mo_4$), macroelements ($NH_4Cl$, $KH_2PO_4$, $MgCl_2$, $CaCl_2$) in order to maintain the best possible bacterial activity;

bicarbonate buffer solution in order to stabilize pH at around 7.0;

the composition to be evaluated, the amount of which is conditioned according to the weight ratio, expressed as dry matter, w(composition)/w(inoculum) =0.3;

water in order to obtain 300m L of useful volume in all the flasks.

In parallel to this, a cold control flask is prepared in order to determine the endogenous activity of the sludges.

The flasks are then placed in a room thermostated at 35° C. with magnetic stirring.

2—Production and analysis of the biogas

At the beginning of the test, the biogas produced is quantified and analyzed each day by gas chromatography. The amounts of methane produced in the biogas and also the $H_2S$ contents are thus determined. The number of samples taken is then re-evaluated as the test progresses according to the methanogenic activity of each flask. The methane potential is determined by dividing the volume of methane produced by the introduced amount of organic matter derived from the sample. The endogenous activity of the inoculum is also deducted in order to take account of the production due only to the sample. The duration of the test is 28 days corresponding to total digestion of the sample.

3—Results

After deduction of the endogenous activity of the sludges, the following results are obtained with regard to the methane potential and the sulfur content:

| Sample | Composition 1 | Composition 2 | Composition 3 |
|---|---|---|---|
| Methane potential (mL $CH_4$/kg of sample) | 158 | 119 | 64 |
| Sulfur content ppmv | 1068 | 850 | 746 |

All the compositions are methanogenic substrates, which allows them to be used for biogas production.

Compositions 1 and 2, which are preferred compositions of the invention, have a methane potential that is even greater than that of composition 3.

The invention claimed is:

1. A composition comprising, relative to its dry matter:
   up to 50% of sorbitan (M) and isosorbide (D);
   at least 50% of anhydrohexitol polymers (P);
   the sum of the constituents (M)+(D)+(P) coming to 100% and said constituents M and D being present according to an M/(M+D) weight ratio ranging from 0.40 to 0.95, wherein the anhydrohexitol polymers are formed by acid-catalyzed dehydration of sorbitol under heat and pressure conditions to provide a mixture followed by distillation of the mixture to achieve said proportions of (M), (D) and (P).

2. The composition as claimed in claim 1, wherein said composition comprises:
   from 5% to 50% of sorbitan (M) and isosorbide (D);
   from 50% to 95% of anhydrohexitol polymers (P).

3. The composition as claimed in claim 1, wherein the constituents (M) and (D) are present according to an (M)/(M+D) weight ratio ranging from 0.42 to 0.90.

4. The composition as claimed in claim 1, wherein the weight percentage of 1,4-sorbitan optionally present in the composition is, relative to the total amount of sorbitan is less than 10%.

5. The composition as claimed in claim 1, wherein said composition has a Brookfield viscosity, according to a test A, included in the range of from 200 to 2000 mPa.s, the test A consisting in adjusting the dry matter of the composition to 85% and then measuring the Brookfield viscosity at 60° C. of the resulting composition.

6. The composition as claimed in claim 1, wherein said composition has a dry matter ranging from 50% to 100%.

7. The composition as claimed in claim 1, wherein said composition has, relative to its dry matter, an amount of sulfur of less than 3%.

8. The composition as claimed in claim 1, wherein said composition has, according to a test B, a freezing point of less than 10° C., the test B consisting in adjusting the dry matter of said composition to 85% and in measuring the freezing point of the composition with the dry matter thus adjusted.

9. A methanization process comprising:
   a step of introduction, into a digester, of a methanogenic substrate comprising a product of internal dehydration of a hydrogenated sugar, in the presence of a microorganism, so as to form a methanogenic medium;
   a step of anaerobic digestion of the methanogenic substrate at a temperature ranging from 15 to 70° in order to form a biogas;
   a step of recovery of said biogas, this step possibly being carried out throughout the digestion step.
   wherein the product of internal dehydration of a hydrogenated sugar comprises the composition of claim 1.

10. The process as claimed in claim 9, wherein the digestion step has a duration ranging up to 8 weeks.

11. The process as claimed in claim 9, wherein the dry matter of the methanogenic medium ranges from 0.1% to 50%.

12. The process as claimed in claim 9, wherein a buffer solution is also introduced into the methanogenic medium in order to carry out the anaerobic digestion step.

13. The process as claimed in claim 9, wherein a solution of trace elements and/or a solution of macroelements is (are) introduced into the methanogenic medium in order to carry out the anaerobic digestion step.

14. The process as claimed in claim 9, wherein the product of internal dehydration of a hydrogenated sugar comprises an amount of sulfur of less than 3%.

15. The process as claimed in claim 9, wherein the product of internal dehydration of a hydrogenated sugar is used as a methanogenic substrate together with at least one additional methanogenic matter different than the product of internal dehydration of a hydrogenated sugar, said additional methanogenic matter possibly being waste of agricultural, food-processing, industrial, household or municipal origin.

16. The process as claimed in claim 9, wherein the product of internal dehydration of a hydrogenated sugar is a mixture which has a Brookfield viscosity, according to a test A, included in the range of from 200 to 2000 mPa.s, the test A consisting in adjusting the dry matter of the composition to 85% and then measuring the Brookfield viscosity at 60° C. of the resulting composition.

17. The process as claimed in claim 9, wherein the product of internal dehydration of a hydrogenated sugar has a methane potential greater than 20 milliliters of methane per gram (m$LCH_4$/g) of dry matter of said product.

* * * * *